United States Patent [19]

Miwa

[11] Patent Number: 4,564,019
[45] Date of Patent: Jan. 14, 1986

[54] METHOD FOR MEASURING CHARACTERISTICS OF LIVING TISSUES BY ULTRASONIC WAVES

[75] Inventor: Hirohide Miwa, Kawasaki, Japan

[73] Assignee: Fujitsu Limited, Kawasaki, Japan

[21] Appl. No.: 480,589

[22] Filed: Mar. 30, 1983

[30] Foreign Application Priority Data

Apr. 7, 1982 [JP] Japan .................................. 57-57573

[51] Int. Cl.$^4$ ............................................... A61B 10/00
[52] U.S. Cl. ...................................... 128/660; 73/599; 73/602
[58] Field of Search ................................ 128/660–663, 128/599; 73/602, 607, 625–626

[56] References Cited

U.S. PATENT DOCUMENTS 4,414,850 11/1983 Miwa et al. ..................... 128/660 X

OTHER PUBLICATIONS

Kuc, R. et al., "Estimating the Acoustic Attenuation Coefficient Slope of a Liver from Reflected UTS Signals", IEEE Trans. SIUS vol. SU-26, Sep. 1979, pp. 353–362.

Dines, K. A. et al., "UTS Attenuation Tomography of Soft Tissue," UTS Imaging vol. 1, #1 1979.

Primary Examiner—William E. Kamm
Assistant Examiner—Francis J. Jaworski
Attorney, Agent, or Firm—Staas & Halsey

[57] ABSTRACT

Ultrasonic waves of at least three independent frequency bands having different center frequencies are transmitted into a living body from its skin surface and reflected waves are analyzed, by which living tissue characteristics are measured. The reflected waves from various depths in the living body are received, their frequency components are separately extracted and energies of the received reflected waves are obtained, thereby obtaining an attenuation coefficient inclination and a space inclination of a frequency power exponent of a reflection coefficient of the living body.

16 Claims, 5 Drawing Figures

11 : Transducer
12 : Driver
13 : Amplifier
14 : Gate
15 : A/D converter
16 : DFFT (Digital Fast Fourier Transformation Circuit)
17-1, 17-2, ⋯ : Calculating Unit
171, 172 : Square Circuit
173 : Adder
174 : Logarithmic Amplifier
175 : Subtractor
176 : Memory
177 : Subtractor
178 : ROM
18-1, 18-2, ⋯ : Subtractor
19-1, 19-2 : Algebraic Calculator
20 : Arithmetic Mean Circuit
21 : Adder
22 : Divider
23 : Register
24 : Arithmetic Mean Circuit
25 : Adder
26 : Divider

METHOD FOR MEASURING CHARACTERISTICS OF LIVING TISSUES BY ULTRASONIC WAVES

BACKGROUND OF THE INVENTION

The present invention relates to a method for measuring characteristic parameters of living tissues by transmitting ultrasonic waves into a living body and analyzing reflected waves therefrom. More particularly, the invention pertains to a method for measuring the frequency dependency of the reflection coefficient and that of the attenuation coefficient of the living tissue separately of each other.

Conventional systems for obtaining tissue characteristics by analyzing reflected ultrasonic waves of plural frequencies have been proposed by Iinuma (Japanese Patent "Kokai" No. 38490/74) and Nakagawa (Japanese Patent Publication No. 24798/77). With these systems, however, their operations are based on sound pressure waveforms, to that when the ultrasonic waves have a wide frequency band, like pulses, accurate measurements are impossible under the influence of the phase relationships of respective frequency components, pulse overlapping of continuous reflected waves and phase cancellation in a receiving sensor.

The abovesaid prior art systems can be employed in the case where the living body is composed of several kinds of tissues, an ultrasonic reflector of a definite, approximately smooth surface exists at the boundary between adjacent tissues and the reflection factor and the transmission factor of the ultrasonic reflector have no frequency dependence. Such reflection is called specular reflection.

With recent technological progress, however, it has become possible to measure a weak reflection from the tissue between boundaries. In general, the tissue has such a microstructure that cells, capillary vessels, lymphatic vessels, muscular fibers and so forth intertwine complicatedly. A typical size of such a tissue is nearly equal to or smaller than the wavelength of ultrasonic waves. On account of this, reflected waves from the microstructure are accompanied by complex interference owing to phase dispersion and pulse overlapping, introducing in a B-mode tomogram a speckled pattern commonly referred to as "speckle". It has been proven experimentally that reflection from the tissue (backward scattering) has a frequency characteristic such that its power reflection coefficient is proportional to the nth power of the frequency, and that the value of n is a characteristic value (a parameter) representing the tissue. It has been reported that n=2.1 to 2.2 in the liver and n=3.3 in the myocardium.

Systems for obtaining the tissue characteristics in such a case have been proposed by Hayakawa in references 1* and 2* and by others.

*1. "Theory of Reflecting Ultrasonic Computer Tomograph Using Plural Frequencies", Proceedings of the 37th meeting of Japan Society of Ultrasonics in Medicine, in Japanese
*2. "Multifrequency echoscopy for quantitative acoustical characterization of living tissues.", J. Acoust. Soc. Am. 96 (6), June 1981.

Noting the energy value of ultrasonic waves, the system *1 conducts a second order differentiation of an attenuation coefficient by the natural logarithm of the frequency ($\partial^2 \alpha / \partial (\ln f)^2$) and a first order differentiation in the direction of depth, by which "a second order differentiated value of the attenuation coefficient of the ultrasonic waves by the natural logarithms of their frequencies" is obtained as a tissue characteristic parameter. According to the system *2, energy (or power) values of the ultrasonic waves are obtained through utilization of three frequencies $f_1$, $f_2$ and $f_3$ and, as a difference value, "the second order differentiated value of the attenuation coefficient of the ultrasonic waves by the natural logarithm of their frequencies" is obtained in the form of a parameter. As experimentally ascertained, it is indicated that, when the attenuation coefficient is proportional to the first power of the frequency, as experimentally ascertained, the abovesaid parameter $$\frac{\partial^2 d}{\partial (\ln f)^2}$$

becomes proportional to the attenuation constant $\alpha$.

The abovesaid Hayakawa system requires complex processing corresponding to the second order differentiation by the natural logarithm of the frequencies, and hence is difficult realtime processing and poor in SN ratio; further, tissue information on the reflection (backward scattering) is entirely lost. Moreover, the parameters thus obtained are insignificant from a physical viewpoint.

SUMMARY OF THE INVENTION

It is an object of the present invention to provide a method which enables separate measurement of tissue characteristic information on the attenuation and reflection coefficients of a living tissue to thereby permit non-invasive measurement of accurate internal living tissue information from the skin surface and which is therefore of great utility when employed for a medical diagnosis, a medical checkup for geriatric diseases and so forth.

Another object of the present invention is to provide a method for obtaining tissue information on not only attenuation but also reflection (backward scattering) coefficients of a living tissue through simple processing which can be executed on a real-time basis and does not introduce much noise.

Another object of the present invention is to provide a method which obtains energy (or power) values of the reflection from a living tissue of ultrasonic waves of at least three frequency bands (or components), and which performs arithmetic processing of the energy values to thereby obtain living tissue characteristic values (parameters) of clear physical meaning, such as a frequency inclination of an attenuation coefficient of a living tissue and a space inclination of a frequency power exponent of its reflection coefficient, through simple processing which can be performed on a real-time basis and does not introduce much noise.

The present invention provides a method in which energies of ultrasonic waves of at least three frequency bands (or components) reflected from a living tissue are obtained, and differences among their logarithms are obtained and then an attenuation inclination and/or reflection power exponent inclination of the living tissue are obtained from at least two equations obtained by differentiating the differences in terms of the depth of measurement.

The "power" mentioned herein is energy per unit time but, in this specification, it is also referred to as the "energy".

BRIEF DESCRIPTION OF THE DRAWINGS

The present invention will be more readily understood by reference to the following detailed description, when considered in conjunction with the accompanying drawings, wherein.

DESCRIPTION OF THE PREFERRED EMBODIMENTS

Figure 1:
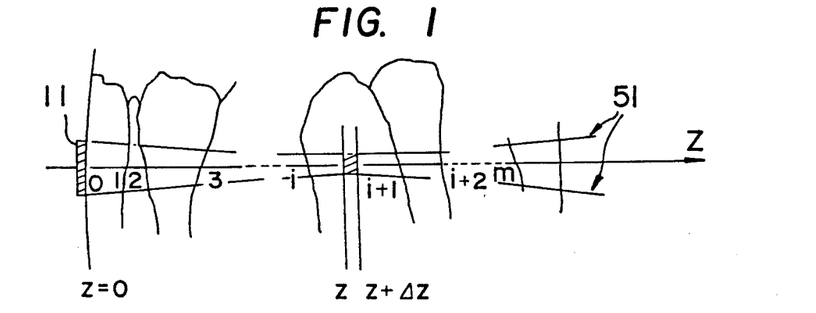
FIG. 1 is a schematic diagram of a three-dimensional model illustrating the manner of actual measurement, explanatory of the principle of the present invention.

A description will be given first, with reference to FIG. 1, of the principle of the present invention. FIG. 1 shows the manner in which an ultrasonic transducer 11 formed by a piezoelectric element, for example, PZT sold by Clevite Inc., held in contact with the skin surface 0 of a living body, transmits thereinto and receives therefrom ultrasonic pulses in a direction Z. Reference numerals 0, 1, 2, ... i, i+1, ... and m indicate boundaries of body tissues crossing the Z-axis. Intermediate portions between adjacent boundaries, for instance, 0-1, 1-2, 2-3, ... i−(i+1), ... show, for instance, the outer skin, fat, muscles, ... the liver, ... and so forth. Reference numeral 51 designates a focused sound field that is determined by the radius of curvature of a concave aperture of the transducer 11 and the frequency of the ultrasonic waves used.

The intensity of received waves reflected from a depth z varies as a function of the depth z with a factor determined by three-dimensional geometric conditions which are dependent on the convergence of a beam both to and from the reflecting portion and the wavelength, such as the degree of focusing, even if the subject under test is not a living body but water or the like which does not attenuate ultrasonic waves. The ratio of the received wave power from the depth z to the same from z=0 is defined as $G_1(z)$. This ratio can be measured by disposing a perfect reflector, such as a metal plate, at the arbitrary depth z and at z=0 in water or the like.

Transmitted ultrasonic waves having reached the boundary i are reflected back or scattered (reflected, refracted) aside three-dimensionally since the living tissues on both sides of the boundary i have different acoustic impedances or the boundary i has irregularities; however, since the acoustic impedance and the speed of sound in the living body do not widely differ with tissues, the transmitted ultrasonic waves mostly pass through the boundary i. Letting the power transmission factor, power reflection factor and power scattering factor of the boundary i with respect to the incident wave power thereon be represented by $\tau_i$, $\gamma_i$ and $\delta_i$, respectively, they bear the following relationships:

$$\tau_i + \gamma_i + \delta_i = 1, \tau_i >> \gamma_i + \delta_i$$

Therefore, even if $\gamma_i$ and $\delta_i$ have some frequency dependence, $\tau_i$ can be regarded as having no frequency dependence.

Figure 2:
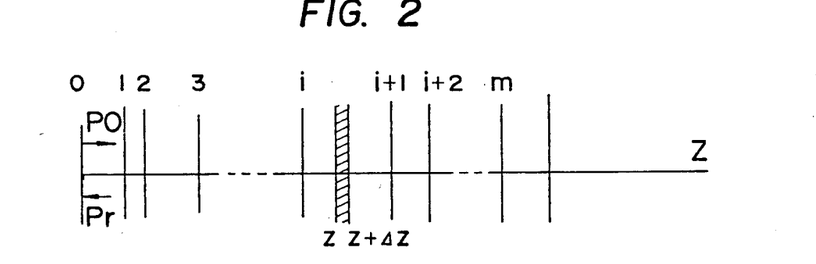
FIG. 2 is a schematic diagram showing a one-dimensional model obtained by a correction of the model of FIG. 1.

Through using corrections by the abovesaid $G_1(z)$ and $\tau_i$, such a three-dimensional model as shown in FIG. 1 can be converted into such a one-dimensional model as shown in FIG. 2. The following description will be given of the one-dimensional model. In FIG. 2 the transducer has indefinite expanses in the X and Y directions normal to the ultrasonic transmission direction Z.

The voluminal tissue sandwiched between the boundaries i and i+1 has a microstructure of a typical size nearly equal to or smaller than the wavelength of the ultrasonic waves and having cells, capillary vessels, fibers, nerves and so forth intertwined complicatedly. The microstructure cannot theoretically be measured because of its size relative to the wavelength of the ultrasonic waves and only a spatial mean value of the microstructure can be measured. It has been proven experimentally that ultrasonic waves transmitted into a living body are subjected to attenuation which varies exponentially as the depth (z) increases, and that its pressure attenuation constant $\alpha$ is proportional to the frequency f of the ultrasonic waves. That is, $$\alpha = \beta f$$

where $\beta$ is a proportional constant. The proportional constant $\beta$ is a frequency inclination of the attenuation constant, it is referred to as an attenuation inclination and it is a characteristic value of the tissue.

A reflection from a voluminal tissue is statistically a speckled reflection commonly referred to as "speckle" and a power reflection coefficient $\gamma$ is given experimentally as follows:

$$\gamma = bf^n$$

where b and n are constants. The constant n is a frequency power exponent of the reflection coefficient and a characteristic value of the tissue.

In FIG. 2, let it be assumed that ultrasonic waves of a frequency $f_1$ (frequency band $2\Omega$, where $\Omega$ is a half-width) are transmitted and corresponding ultrasonic waves are received. Alternatively, it may also be assumed that pulses of a wide frequency band are transmitted, the amplitude of a component of the frequency $f_1$ is $Q_1(0)$ and the component of the frequency $f_1$ of reflected waves is observed. Letting the time gain control amplification degree (TGC) of the received signal and the apparent energy observed including the time gain control amplification degree (TGC) be represented by $A_1(z)$ and $E_1(z)$, respectively, $E_1(z)$ is given by the following equation. For convenience of description, the following expression is a computational expression obtained from sound pressure measurement but, if the power of the waves can be directly measured, a direct representing expression can be used.

$$E_1(z) = Q_1^2(0) \left( \sum_{i=0}^{j} \tau_i \tau_i' \right) \cdot A_1^2(z) \cdot G_1(z) \cdot b(z) \cdot f_1^{n(z)} \quad (1)$$

$$e^{-4f \int_0^z \beta(z)dz} \cdot F(f_1 \cdot z)$$

where $F(f_1 \cdot z)$ is a correcting term obtained by integrating frequency dependent components of reflection and attenuation in connection with a frequency variation from $f_1$ in the band $2\Omega$. When $\Omega << f_1$, $F(f_1, z)$ can be regarded as invariable at the frequency $f_1$. $\tau_i'$ is the transmission factor of the reflected waves at the boundary i. $\pi$ indicates multiplications of $\tau_i \tau_i'$ from i=0 to i=j. The upper limit J on i is a maximum number from the skin surface to the depth z.

Apparent energy $E_2$ similarly observed in respect of a sound frequency $f_2$ is as follows:

$$E_2(z) = Q_2^2(0) \left( \sum_{i=0}^{j} \tau_i \tau_i' \right) \cdot A_2^2(z) \cdot G_2(z) \cdot b(z) \cdot f_2^{n(z)}. \quad (2)$$

$$e^{-4/2} \int_0^z \beta(z)dz \cdot F(f_2 \cdot z);$$

When $\Omega_1 << f_1$ and $\Omega_2 << f_2$, it can be regarded that $F(f_1, z) = F(f_2, z)$, where $\Omega_1$ and $\Omega_2$ are half-widths.

The difference between the natural logarithms of Eqs. (1) so that (2) is as follows:

$$\ln \frac{E_1(z)}{E_2(z)} = 2 \left( \ln \frac{Q_1(0)}{Q_2(0)} + \ln \frac{A_1(z)}{A_2(z)} + \ln \frac{G_1(z)}{G_2(z)} + \right. \quad (3)$$

$$\left. n(z)\ln \frac{f_1}{f_2} - 4(f_1 - f_2) \int_0^z \beta(z)dz \right)$$

Differentiating (or differencing) Eq. (3) with respect to the depth z (in a reflected signal train, $z=ct$, where c is the sound speed, and Eq. (3) may also be differentiated with respect to time t), it follows that $$\frac{\partial}{\partial z} \left[ \ln \frac{E_1(z)}{E_2(z)} - 2\ln \frac{A_1(z)}{A_2(z)} - 2\ln \frac{G_1(z)}{G_2(z)} \right] = \quad (4)$$

$$\frac{\partial n(z)}{\partial z} \ln \frac{f_1}{f_2} - 4(f_1 - f_2)\beta(z)$$

Similarly setting up the equation corresponding to Eq. (4) with respect of $f_2$ and $f_3$ by introducing a third frequency $f_3$, it follows that $$\frac{\partial}{\partial z} \left[ \ln \frac{E_2(z)}{E_3(z)} - 2\ln \frac{A^2(z)}{A_3(z)} - \ln \frac{G_2(z)}{G_3(z)} \right] = \quad (5)$$

$$\frac{\partial n(z)}{\partial z} \ln \frac{f_2}{f_3} - 4(f_2 - f_3)\beta(z)$$

In Eqs. (4) and (5), $E_1$, $E_2$ and $E_3$ are measured as functions of the depth z.

Accordingly, the left sides of Eqs. (4) and (5) are both measured values.

The left sides of Eqs. (4) and (5) can be transformed as follows:

$$\left. \begin{array}{c} \frac{\partial}{\partial z} \left[ \ln \frac{E_1}{G_1 A_1^2} - \ln \frac{E_2}{G_2 A_2^2} \right] \\ \text{and} \\ \frac{\partial}{\partial z} \left[ \ln \frac{E_2}{G_2 A_2^2} - \ln \frac{E_3}{G_3 A_3^2} \right] \end{array} \right\} \quad (6)$$

where $$\frac{E_i}{G_i A_i^2}$$

corresponds to true energy obtained by correcting the apparent observed energy $E_i$.

On the right sides of Eqs. (4) and (5), $$\frac{\partial n(z)}{\partial z}$$

and $\beta(z)$ are unknown and $f_1$, $f_2$ and $f_3$ in the coefficients are known. Accordingly, from the simultaneous algebraic equations of Eqs. (4) and (5), namely: the two unknowns $\beta(z)$: frequency inclination of attenuation coefficient, and $$\frac{\partial n(z)}{\partial z} :$$

space inclination of frequency power exponent of reflection coefficient, can be obtained as functions of the depth z.

The above is a description of the principle of the present invention. The present invention is free from the influence of the boundary transmission factors $\tau_i$ and $\tau'_i$, the constant $(b)z$ of the reflection coefficient and the absolute values $Q_1$, $Q_2$ and $Q_3$ of the amplitudes of respective frequency components. While in the foregoing Eq. (5) is set up using $f_2$ and $f_3$, it may also be set up using $f_3$ and $f_4$. Furthermore, if the value A of the time gain control amplification degree (TGC) is held constant with respect to all frequencies, then $$\ln \frac{A_1}{A_2}$$

and $$\ln \frac{A_2}{A_3}$$

become zero, making compensation unnecessary.

Eq. (1) and so on can be represented using the amplitude absolute value $Q_i(z)$ of the sound pressure but, in order to avoid a bad influence of the phase term, it is necessary to obtain $E_i$ first and then $Q_i$ from $$Q_i(z) = \sqrt{E_i(z)}$$

This is not so significant, and hence is not described in this specification.

By putting the three frequencies $f_1$, $f_2$ and $f_3$ into a geometric progression, the subsequent calculations are simplified. Letting $$\frac{f_1}{f_2} = \frac{f_2}{f_3} = s \quad (7)$$

the right sides of Eqs. (4) and (5) respectively become as follows:

$$\frac{\partial n(z)}{\partial z} \ln s - 4f_2(s - 1)\beta(z) \quad (8)$$

$$\frac{\partial n(z)}{\partial z} \ln s - 4f_2 \left(1 - \frac{1}{s}\right) \beta(z) \quad (9)$$

Furthermore, obtaining a difference between Eqs. (4) and (5), the term $$\frac{\partial n(z)}{\partial z}$$

is eliminated as will be seen from Eqs. (8) and (9). That is, $$\frac{\partial}{\partial z}\left[\ln \frac{E_1(z)}{E_2(z)} - 2\ln \frac{A_1(z)}{A_2(z)} - \ln \frac{G_1(z)}{G_2(z)}\right] - \quad (10)$$

$$\frac{\partial}{\partial z}\left[\ln \frac{E_2(z)}{E_3(z)} - 2\ln \frac{A_2(z)}{A_3(z)} - \ln \frac{G_2(z)}{G_3(z)}\right] =$$

$$4f_2\left(2 - \frac{1}{s} - s\right)\beta(z)$$

Thus the calculation for obtaining $\beta(z)$ is simplified.

Also the calculation is simplified by putting the frequencies $f_1$, $f_2$ and $f_3$ into an arithmetic progression, that is, $$f_1 - f_2 = f_2 - f_3 \quad (11)$$

In this case, when obtaining the difference between Eqs. (4) and (5), $\beta(z)$ is eliminated and $$\frac{\partial n(z)}{\partial z}$$

can be obtained easily.

Since the pulse length of reflected waves from the depth z usually has a finite value that is not 0, the reflected waves are superimposed on reflected waves from irregular tissues before and after the depth z and certain frequency components may sometimes be irregularly added to or subtracted from each other due to interference, leading to a noticeable error. This is called spectrum scalloping. To avoid this, it is preferable that N different values for $\beta(z)$ and $$\frac{\partial n(z)}{\partial z}$$

obtained by the above-described method be subjected to statistical processing through utilization of as many combinations of frequency components as possible in a utilizable frequency band, for example, for N frequency components $f_{j1}$, $f_{j2}$ and $f_3$ (for each $j=0$ to N) thereby obtain their mean values for the respective frequency band.

It is needless to say that the calculations for obtaining $\beta(z)$ and $$\frac{\partial n(z)}{\partial z}$$

can be simplified by using the frequencies in the form of a geometric or arithmetic progression.

For improving the statistical precision, it is also possible to transmit and receive pulses and to measure them M times for the same scanning line and to perform statistical processing of the measured values, of various quantities during computation and of the final computed values. For instance, even if an examinee holds his breath during measurement, tissues on the scanning line wobble three-dimensionally owing to pulsation of the heart, small changes in his posture and so forth. Accordingly, observed values at the depth z in the M-times measurement are distributed in a specific space domain around a mean center X·Y·Z and the M-times statistical processing bears the same meaning as statistical processing of measured values at M measuring points in a certain space domain. By conducting the statistical processing in connection with L points before and after the depth z for each scanning, the statistical accuracy is further improved.

By this, a maximum of $L \times M \times N$ samples can be obtained.

If the tissue characteristic value thus obtained as a function of the depth z on a certain scanning line is displayed on the corresponding scanning line on a CRT or the like as in the case of a B-mode graph, a two-dimensionally or three-dimensionally distributed image can be obtained. This is useful for finding out an abnormality, such as a cancer or the like, by visual examination.

Figure 3A:
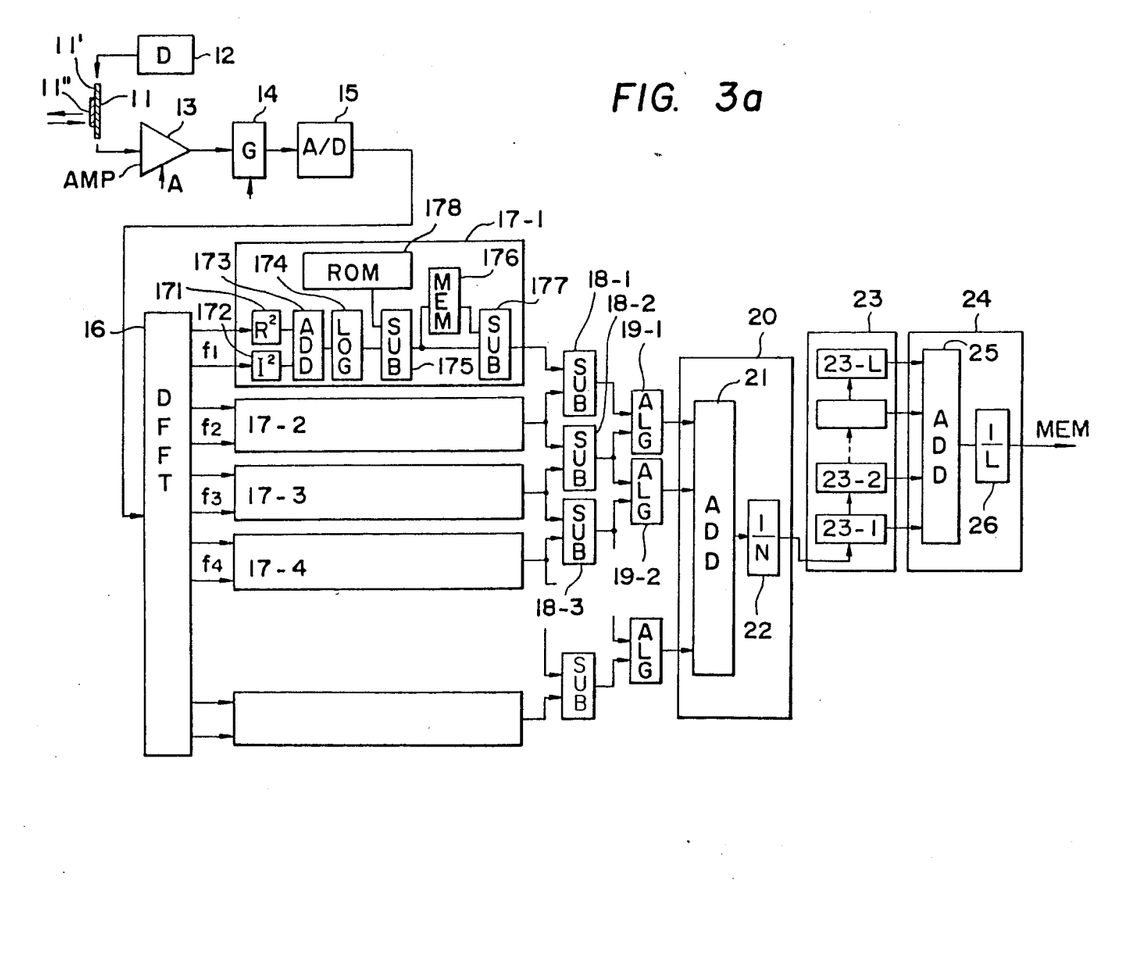
FIG. 3a is a block diagram illustrating an embodiment of the present invention with the components identified in FIG. 3b.
Figure 3B:
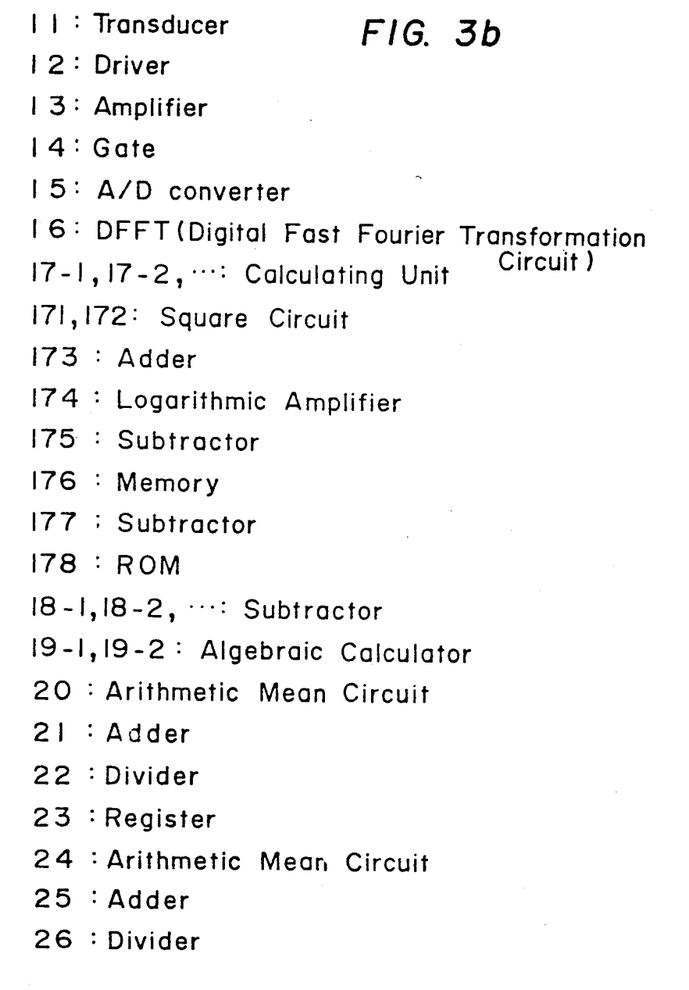
Figure 4:
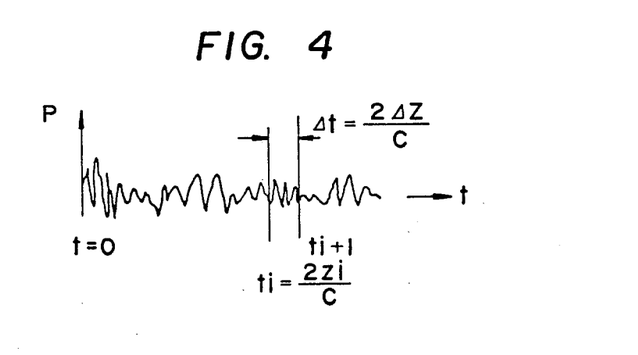
FIG. 4 is a time domain diagram of a received reflected signal.

A description will be given of the method of the present invention. FIG. 3 illustrates an example of apparatus suitable for carrying the present invention into practice. In FIG. 3 reference numeral 11 indicates a wide-band transducer, which is formed by piezoelectric elements of the aforementioned PZT or PVDF (polyvinylidene fluoride sold by Kureha Kogyo of Japan). The transducer 11 is shown to be a compound transducer which comprises a PZT transducer 11' and PVDF transducer 11" covering different frequency bands. It is also possible to employ such a system in which the transducer is formed by three layers of center frequencies $f_1$, $f_2$ and $f_3$ for covering frequency bands $2\Omega_1$, $2\Omega_2$ and $2\Omega_3$ (where $\Omega_1$, $\Omega_2$ and $\Omega_3$ are half-widths), respectively, and received waves are separated by filters to obtain energies $E_1$, $E_2$ and $E_3$. In this illustrated example, however, pulses of wide band are transmitted and the DFFT (Digital Fast Fourier Transformation) is used. Reference numeral 12 designates a driver, which may be arranged to drive the transducers 11' and 11" by impulses or in separately specified frequency bands. Reference numeral 13 identifies a wide-band amplifier for amplifying signals of received reflected waves. The received signal varies with time as shown in FIG. 4 with the time of transmission of pulses represented by $t=0$, and signals are reflected back from deeper positions in a living body with the lapse of time. The reflected wave from a depth $z_i$ appears at such a time as follows:

$$t_i = 2z_i/C \quad (12)$$

where C is the sound speed in the living body. A signal from a tissue between the depth $z_i$ and $z_i + \Delta z$ appears in the following time interval:

$$\Delta t = \frac{2\Delta z}{C} \quad (13)$$

Accordingly, the tissue characteristic between the depths $z_i$ and $z_i + \Delta z$ can be obtained by analyzing the signal received in the time interval $\Delta t$.

Since the reflected signal decreases exponentially with an increase in the depth z by virtue of attenuation on forward and backward paths, the amplification degree A of the amplifier 13 is varied with an increase in the depth z or with the lapse of time t. This is called time-gain control or sensitivity-time control. This control is needed for retaining excellent SN ratio in subsequent signal processing.

Reference numeral 14 denotes a gate, which is opened in the time phase of Eq. (12) and closed after the lapse of time given by Eq. (13). Reference numeral 15 represents an A/D converter, which is required to have a sampling speed of about 20 MHz for signals of 1 to 10 MHz band. Assuming that $\Delta z = 1.5$ mm, then $C = 1500$ m/s, so that $\Delta t = 2$ μs and, if sampling is carried out at 20 MHz, about 40 samples (2 μs/(1/20 MHz)) for each measuring point can be obtained. A plurality of such measuring points is provided along each scanning line.

Reference numeral 16 shows a DFFT (Digital Fast Fourier Transformation) circuit, which analyzes the abovesaid 40 data to output real parts and imaginary parts of about 50 frequency components. For instance, in the case of the frequency $f_1$, a component in-phase with $\cos 2\pi f_1 t$ is a real part $R_1$ and a component in-phase with $\sin 2\pi f_1 t$ is an imaginary part $I_1$.

Reference numerals 17-1, 17-2, ... refer to calculating units, which are supplied with the real parts and the imaginary parts of components of the frequencies $f_1$, $f_2$, $f_3$, $f_4$, ... from the DFFT circuit 16. Since the calculating units 17-1, 17-2, ... are identical in construction and in operation, a detailed description will be given of the calculating unit 17-1 alone.

The calculating unit 17-1 receives the real part $R_1$ and the imaginary part $I_1$ of the frequency $f_1$ from the DFFT circuit 16. The real part $R_1$ and the imaginary part $I_1$ are squared by square circuits 171 and 172 to obtain $R_1^2$ and $I_1^2$, which are added by an adder 173, obtaining the sum $R_1^2 + I_1^2$. This sum is equal to $E_1$. Next, $\ln E_1$ is obtained by a logarithmic amplifier 74. Further, $\ln G_1 \cdot A_1^2$ is obtained as a function of the depth z (or the time t) and prestored in the form of a table in a ROM 178, from which is read out a value for the corresponding z (or t). The output $\ln E_1$ of the logarithmic amplifier 174 and the output $\ln F_1^2 \cdot A_1^2$ of the ROM 178 are applied to a subtractor 175, wherein a subtraction $\ln E_1 - \ln G_1 \cdot A_1^2$ is carried out to output $$\left[\ln \frac{E_1}{G_1 \cdot A_1^2}\right]_{t=t_i},$$

which is stored in a memory 176.

Similar processing is performed for the reflected signal received at a time $t_i + 1$ after $\Delta t$ to obtain $$\left[\ln \frac{E_1}{G_1 \cdot A_1^2}\right]_{t=t_i+1},$$

and a difference between this and $$\left[\ln \frac{E_1}{G_1 \cdot A_1^2}\right]_{t=t_i}$$

at the time $t_i$ stored in the memory 176 is obtained by a subtractor 177. The difference thus obtained is a differentiated (differenced) value at $\Delta z$. This becomes the output of the calculating unit 17-1 and represents the following quantity:

$$-\frac{\partial}{\partial z}\ln\left(\frac{E_1}{G_1 \cdot A_1^2}\right) \qquad (14)$$

Likewise, the calculating unit 17-2 provides the following output:

$$-\frac{\partial}{\partial z}\ln\frac{E_2}{G_1 \cdot A_1^2} \qquad (15)$$

Reference numerals 18-1, 18-2, 18-3, ... signify subtractors. The subtractor 18-1 subtracts the output of the calculating unit 17-2 from the output of the calculating unit 17-1. The subtractor 18-2 subtracts the output of the calculating unit 17-3 from the output of the calculating unit 17-2. The other subtractors operate in a similar manner. In a similar manner, the following subtractors operate.

Thus the output of the subtractor 18-1 provides the difference between Eqs. (14) and (15):

$$-\frac{\partial}{\partial z}\left(\ln\frac{E_2}{G_1 \cdot A_1^2} - \ln\frac{E_2}{G_2 \cdot A_2^2}\right) \qquad (16)$$

This is the left side of Eq. (4) as shown in Eq. (6). The order of calculation by the calculating units 17-1 and 17-2 and the calculation by the subtractor 18-1 is reverse from the order of calculations described previously but, in this case, it does not matter mathematically.

The output of the subtractor 18-2 similarly provides the left side of Eq. (5).

Reference numeral 19-1 indicates an algebraic calculator which receives the outputs of the subtractors 18-1 and 18-2 and solves from Eqs. (4) and (5) a simultaneous equation with $\beta(z)$ and $$\frac{\partial n(z)}{\partial z}$$

as the unknowns. Certain constants $\alpha_{11}$ and $\alpha_{12}$ determined by the frequencies $f_1$ and $f_2$ are multiplied by the outputs of the subtractors 18-1 and 18-2 and then added together to obtain $\beta(z)$. Other constants $\alpha_{21}$ and $\alpha_{22}$ are likewise multiplied by the outputs of the subtractors 18-1 and 18-2 and then added together to obtain $$\frac{\partial n(z)}{\partial z}.$$

It is convenient to calculate the constants $\alpha_{11}$, $\alpha_{12}$, $\alpha_{21}$ and $\alpha_{22}$ from the frequencies $f_1$ and $f_2$ in advance and to prestore them in the algebraic calculator 19-1.

Reference numeral 20 designates an arithmetic mean circuit which comprises an adder 21 for adding the outputs of the algebraic calculators 19-1, 19-2, ... and a divider 22 for dividing the output of the adder 21 by the number N of inputs to the adder 22. The arithmetic mean circuit 20 obtains an arithmetic mean value of the N $\beta(z)$ or $$\frac{\partial n(z)}{\partial z}$$

values respectfully obtained from all the frequency components of the output from the DFFT circuit 16.

Reference numeral 23 identifies a shift register which comprises L stacked registers 23-1, 23-2, ... 23-L for storing the output of the arithmetic mean circuit 20. At first, the output of the arithmetic mean circuit 20 for the depth i is written into the register 23-1 and when the output of the arithmetic mean circuit 20 for the next depth goes into the register 23-1, the content of the register 23-1 is shifted to the register 23-2. In this way, upon each occurrence of inputting new data into the register 23-1, previous data are shifted upward through successive registers in the shift register 23. In consequence, L data are stored in the shift register 23, with the oldest data in the register 23-L and the latest one in the register 23-1.

Reference numeral 24 denotes an arithmetic mean circuit for obtaining an arithmetic mean value of L data. The arithmetic mean circuit 24 is also comprised of an adder 25 for adding L outputs from the registers 23-1 to 23-L and a divider 26 for dividing the output of the adder 25 by L. The outputs of the registers 23-1 to 23-L are added together by the adder 25 and its output is applied to the divider 26, wherein it is divided by L to obtain the arithmetic mean.

The output of the arithmetic mean circuit 24 provides, for each scanning, a mean value of (L×Z) $\beta(z)$'s or $$\frac{\partial n(z)}{\partial n}\text{'s}$$

over the depths $z_1, z_2, z_3, \ldots Z_L$ is obtained, and the mean value is stored in a memory. By scanning the same tissue M times at certain time intervals, obtaining a measured value for each scanning, storing it and averaging the values for the same depth $z_i$ in all the measurements, it is possible to obtain a mean value of L×M×N samples for each depth $z_i$.

While the above description has been given of a method for executing statistical processing with the last calculated value $\beta(z)$ or $$\frac{\partial n(z)}{\partial z},$$

the statistical processing can be applied to intermediate results and this may sometimes make the subsequent calculations easy. This can be achieved, for example, by executing statistical processing of the outputs of the DFFT circuit 16 in connection with frequency for M-time scanning of L points to remove the influence of the spectrum scalloping and executing again statistical processing with a last calculated value.

In the foregoing embodiment the frequency components $f_1, f_2, f_3, \ldots$ correspond to the outputs of the DFFT circuit 16 in a sequential order but, by a suitable selection of the outputs of the DFFT circuit 16 in a manner to form a geometric or arithmetic progression as described previously, the calculating circuits of the algebraic calculators 19-1, 19-2, ... can be simplified although the number of N's decreases.

By scanning one sectional area of a living body in successive scanning directions so that, for instance, $\beta(z)$ may be obtained as a function of each of the depths $z_1, z_2, \ldots z_i$ and $z_{i+1}$ as a mean value of the L×M×N measured values for each scanning direction, and then displaying the resulting values on the corresponding scanning lines of a CRT, it is possible to obtain a distribution diagram of $\beta(z)$ or $$\frac{\partial n(z)}{\partial z}$$

on the sectional area of the living body. This is very useful for detecting an abnormal tissue as of a cancer.

It will be apparent that many modifications and variations may be effected without departing from the scope of the novel concepts of the present invention.

What is claimed is:

1. A method for measuring the internal characteristics of a body, comprising:
    transmitting pulses of ultrasound pressure waves into said body, each said pulse comprising ultrasound pressure waves of at least three frequencies;
    selectively receiving as different respective return signals the corresponding ultrasound pressure waves reflected from different ranges of depths in said body;
    determining values corresponding to the relative energy of respective frequency components in each said return signal corresponding to said at least three frequencies; and
    processing said values to determine information on spatial variation of the reflection coefficient at different depths in said body.

2. The method of claim 1, said processing involving forming the differences in time in numbers corresponding to said values for adjacent ranges of depth for each respective return signal, and between numbers corresponding to said values for pairs of said frequency components for each respective return signal.

3. The method of claim 2, wherein the reflection coefficient is given by $\delta = bf^n$, and the determining of the variation in the reflection coefficient is in terms of the spatial variation of the frequency power exponent n, b being a constant and f the frequency of the respective ultrasonic waves.

4. The method of claim 2, said processing providing also information on spatial variation of the frequency inclination $\beta$ of the attenuation coefficient $\alpha = \beta f$ in said body, f being the frequency of the respective ultrasonic waves.

5. The method of claim 2 or 4, said processing comprising taking the logarithm of each said value of each respective return signal, prior to forming said differences, and subsequently, after forming said differences, solving algebraically between the respective differences, or selected pairs of said frequency components, to provide the respective information.

6. The method of claim 5, wherein said at least three frequencies define a geometric progression.

7. The method of claim 5, wherein said at least three frequencies define an arithmetic progression.

8. The method of claim 5, comprising averaging the respective results of said solving for said information for different respective pairs of said frequency components.

9. The method of claim 5, comprising performing said processing of said return signals for a plurality of adjacent depths, in said body, and averaging the respective results thus obtained for said information.

10. The method of claim 1 or 4, said processing occurring on a real time basis.

11. The method of claim 1, comprising providing said pulses of ultrasound pressure waves for transmission into said body as broadband pulses including said at least three frequencies, and performing Fourier transformation of each of said return signals for said determining of said values corresponding to the energy of the respective frequency components.

12. A device comprising:
means for transmitting pulses of ultrasonic waves of at least three frequencies into a body under test, and for determining values corresponding to the energies of respective frequency components of corresponding ultrasonic waves reflected from selected ranges of depths in the interior of said body;
means for processing said values to provide information on spatial variation of the reflection coefficient $\delta = bf^n$ within said body, wherein b is a constant, f is the frequency of the respective ultrasonic waves and n is a number.

13. The device of claim 12, said means for processing comprising:
a plurality of calculating units for processing respective ones of said values corresponding to energy of the respective frequency components;
a plurality of subtractors having as inputs the outputs of respective pairs of said calculation units,
a plurality of algebraic units having as inputs the respective outputs of two of said subtractors, and
an arithmetic mean circuit having as inputs the outputs of said algebraic units.

14. The device of claim 13, comprising:
a register for storing in successive stages the successive outputs of said arithmetic means circuit, each said stage providing a respective output of the content stored therein; and
an averaging circuit for averaging the respective outputs of the stages of said register.

15. The device of claim 12, comprising means for providing said values as the logarithm of said energies.

16. The device of claim 12, said processing means including means for providing information on spatial variation of the frequency inclination $\beta$ of the attenuation coefficient $\alpha = \beta f$, where f is the frequency of the respective ultrasonic waves.

* * * * *